United States Patent
Stenzler et al.

(10) Patent No.: US 11,707,432 B2
(45) Date of Patent: Jul. 25, 2023

(54) SYSTEM AND METHOD FOR CONTROLLING THE HARSHNESS OF NICOTINE-BASED DRY POWDER FORMULATIONS

(71) Applicant: PHILIP MORRIS PRODUCTS S.A., Neuchâtel (CH)

(72) Inventors: Alex Stenzler, Long Beach, CA (US); Noe Zamel, Toronto (CA); Arthur Slutsky, Toronto (CA); Steven Ellis, Oro-Medonte (CA); Steve Han, Huntington Beach, CA (US)

(73) Assignee: Philip Morris Products S.A., Neuchâtel (CH)

( * ) Notice: Subject to any disclaimer, the term of this patent is extended or adjusted under 35 U.S.C. 154(b) by 130 days.

(21) Appl. No.: 16/521,913

(22) Filed: Jul. 25, 2019

(65) Prior Publication Data
US 2019/0343178 A1    Nov. 14, 2019

Related U.S. Application Data

(62) Division of application No. 14/856,116, filed on Sep. 16, 2015, now abandoned.

(51) Int. Cl.
  *A61K 9/00*    (2006.01)
  *A61K 31/465*  (2006.01)
  *A24F 42/20*   (2020.01)

(52) U.S. Cl.
  CPC .......... *A61K 9/0075* (2013.01); *A24F 42/20* (2020.01); *A61K 31/465* (2013.01)

(58) Field of Classification Search
  None
  See application file for complete search history.

(56) References Cited

U.S. PATENT DOCUMENTS

| | | | |
|---|---|---|---|
| 5,746,227 A | 5/1998 | Rose et al. | |
| 6,234,169 B1 | 5/2001 | Bulbrook et al. | |
| 6,799,576 B2 | 10/2004 | Farr | |
| 8,182,838 B2 | 5/2012 | Morton et al. | |

(Continued)

FOREIGN PATENT DOCUMENTS

| | | |
|---|---|---|
| CA | 2146954 | 10/1996 |
| CA | 2265198 | 9/1999 |

(Continued)

OTHER PUBLICATIONS

Benowitz et al., 2009, "Nicotine Chemistry, Metabolism, Kinetics and Biomarkers. Hanb. Ex. Pharmacol.," (192): 29-60.

(Continued)

*Primary Examiner* — Kelly M Gambetta
*Assistant Examiner* — Katherine A Will
(74) *Attorney, Agent, or Firm* — Mueting Raasch Group

(57) ABSTRACT

A method of controlling or electing the harshness of inhaled nicotine powder formulations is described. The method includes the steps of identifying a concentration of nicotine for a subject to inhale to achieve a desired level of harshness per inhalation, identifying the total dose of nicotine to be inhaled by the subject, and providing the subject with an amount of a formulation comprising nicotine particles having the identified concentration of nicotine, such that the total amount of nicotine particles in the formulation equals the total dose of nicotine.

14 Claims, 8 Drawing Sheets

| Formulation | Total Dose of Nicotine | Total amount of formulation | Concentration of nicotine | Expected Number of Inhalations | Amount of Nicotine per Inhalation | Resulting Harshness |
|---|---|---|---|---|---|---|
| 7 | 1 mg | 10 mg | 10% | 10 | 0.10 mg | Initial Level Harshness |
| 8 | 0.8 mg | 7 mg | 11.4% | 7 | 0.114 mg | Increased Level Harshness |
| 9 | 0.6 mg | 5 mg | 12% | 5 | 0.12 mg | Increased Level Harshness |

(56) References Cited

U.S. PATENT DOCUMENTS

| | | |
|---|---|---|
| 8,256,433 B2 | 9/2012 | Gonda |
| 8,381,739 B2 | 2/2013 | Gonda |
| 8,440,231 B2 | 5/2013 | Smyth et al. |
| 8,668,934 B2 | 3/2014 | Vehring et al. |
| 8,689,803 B2 | 4/2014 | Gonda |
| 8,741,348 B2 | 6/2014 | Hansson et al. |
| 2001/0026788 A1* | 10/2001 | Piskorz ............... A61K 31/44 424/46 |
| 2003/0103908 A1 | 6/2003 | Piskorz |
| 2003/0186843 A1 | 10/2003 | Staniforth et al. |
| 2006/0018840 A1* | 1/2006 | Lechuga-Ballesteros ................. A01N 43/40 514/343 |
| 2006/0178394 A1 | 8/2006 | Staniforth |
| 2007/0292519 A1 | 12/2007 | Piskorz |
| 2008/0020048 A1 | 1/2008 | Snape et al. |
| 2011/0082076 A1 | 4/2011 | Dellamary et al. |
| 2011/0268809 A1 | 11/2011 | Brinkley et al. |
| 2012/0042886 A1* | 2/2012 | Piskorz ............... A61K 31/44 131/369 |
| 2012/0138056 A1 | 6/2012 | Morton et al. |
| 2013/0098377 A1 | 4/2013 | Borschke et al. |
| 2013/0209540 A1 | 8/2013 | Duggins et al. |
| 2013/0323179 A1 | 12/2013 | Popov et al. |
| 2014/0014106 A1* | 1/2014 | Smutney ............. A61M 15/00 128/203.15 |
| 2014/0079782 A1 | 3/2014 | York et al. |
| 2014/0166027 A1 | 6/2014 | Fuisz et al. |
| 2014/0212504 A1 | 7/2014 | Weers et al. |
| 2014/0234392 A1 | 8/2014 | Hansson et al. |
| 2014/0242174 A1 | 8/2014 | Walker |
| 2014/0261474 A1 | 9/2014 | Gonda |
| 2015/0031609 A1 | 1/2015 | Steiner et al. |

FOREIGN PATENT DOCUMENTS

| | | |
|---|---|---|
| EP | 1732515 B1 | 7/2008 |
| JP | 2011506589 A | 3/2011 |
| JP | 2013/082660 A | 5/2013 |
| JP | 2013-144157 A | 7/2013 |
| WO | WO 2005/107872 | 11/2005 |
| WO | WO 2009/081107 A1 | 7/2009 |
| WO | WO 2015/166344 | 11/2015 |
| WO | WO 2015/166350 | 11/2015 |

OTHER PUBLICATIONS

International Preliminary Report on Patentability, issued by the International Bureau of WIPO for PCT/US2016/051959, dated Mar. 29, 2018; 10 pgs.

Japanese Office Action for JP 2018-514439, issued by the Japanese Patent Office dated Aug. 31, 2020; 10 pgs. including English Translation.

* cited by examiner

| Formulation | Total Dose of Nicotine | Total amount of formulation | Concentration of nicotine | Expected Number of Inhalations | Amount of Nicotine per Inhalation | Resulting Harshness |
|---|---|---|---|---|---|---|
| 1 | 1 mg | 10 mg | 10% | 10 | 0.10 mg | Base Level Harshness |
| 2 | 1 mg | 20 mg | 5% | 20 | 0.05 mg | Decreased Harshness |
| 3 | 1 mg | 5 mg | 20% | 5 | 0.20 mg | Increased Harshness |

Figure 1

| Formulation | Total Dose of Nicotine | Total amount of formulation | Concentration of nicotine | Expected Number of Inhalations | Amount of Nicotine per Inhalation | Resulting Harshness |
|---|---|---|---|---|---|---|
| 4 | 1 mg | 10 mg | 10% | 10 | 0.10 mg | Desired Level Harshness |
| 5 | 0.8 mg | 8 mg | 10% | 8 | 0.10 mg | Desired Level Harshness |
| 6 | 0.6 mg | 6 mg | 10% | 6 | 0.10 mg | Desired Level Harshness |

Figure 2

| Formulation | Total Dose of Nicotine | Total amount of formulation | Concentration of nicotine | Expected Number of Inhalations | Amount of Nicotine per Inhalation | Resulting Harshness |
|---|---|---|---|---|---|---|
| 7 | 1 mg | 10 mg | 10% | 10 | 0.10 mg | Initial Level Harshness |
| 8 | 0.8 mg | 7 mg | 11.4% | 7 | 0.114 mg | Increased Level Harshness |
| 9 | 0.6 mg | 5 mg | 12% | 5 | 0.12 mg | Increased Level Harshness |

Figure 3

SYSTEM AND METHOD FOR CONTROLLING THE HARSHNESS OF NICOTINE-BASED DRY POWDER FORMULATIONS

CROSS-REFERENCE RELATED APPLICATIONS

This is a divisional application of U.S. patent application Ser. No. 14/856,116, filed 16 Sep. 2015, the disclosure of which is incorporated herein by reference thereto.

BACKGROUND OF THE INVENTION

It is well known that inhaled cigarette smoke causes airway irritation and cough, due largely to the fact that nicotine is one of the most common inhaled irritants to the human respiratory tract. This irritation results in a sensation of harshness when nicotine is inhaled by a subject. Depending on the amount of nicotine inhaled during inhalation and the frequency of nicotine inhalation over time, a subject may develop a degree of tolerance to the harshness experienced. Accordingly, the level of harshness tolerated, or preferred, during nicotine inhalation can be very different from one subject to the next.

Most regular smokers become addicted to, or dependent upon, the pharmacological effects of nicotine in tobacco smoke. A common strategy in overcoming nicotine addiction in general, and nicotine cravings in particular, is the mimicking of cigarette smoking's effects, followed by gradual reduction and, eventually, by complete elimination.

There are several effects of smoking which a potential therapeutic formulation or method would seek to mimic. Among the most important effects of smoking are the chemical and mechanical impact of cigarette smoke on airway receptors of the subject, and the absorption of nicotine into the subject's blood. The chemical and mechanical impact of cigarette smoke on the airways of the subject results in a certain level of satisfaction experienced by the subject, and it is also associated with the perceived harshness of the smoke inhalation upon the airways of the subject. The absorption of nicotine into the subject's blood results in nicotine reaching various receptors in the central nervous system of the subject, which in turn affects the perceived nicotine cravings experienced by the subject. Both effects can potentially be mimicked by the administration of nicotine formulation doses to a subject seeking smoking cessation therapy. By gradually reducing the doses, until complete elimination, nicotine addiction can be treated.

There is a need in the art for methods of delivering nicotine-based dry powder formulations which can achieve effective blood nicotine concentrations while at the same time allowing for controlling the satisfaction and harshness of the chemo-mechanical impact of the formulations on the airways of the subject. Ideally, such methods of delivery and harshness control would provide flexibility in delivering the necessary amount of nicotine, while at the same time allowing for a modulation on the degree of harshness experienced by the subject. The present invention satisfies this need.

SUMMARY OF THE INVENTION

A method of controlling the harshness of inhaled nicotine is described. The method comprises the steps of identifying a concentration of nicotine for a subject to inhale to achieve a desired level of harshness per inhalation, identifying the total dose of nicotine to be inhaled by the subject, and providing the subject with an amount of a formulation comprising nicotine particles having the identified concentration of nicotine, such that the total amount of nicotine particles in the formulation equals the total dose of nicotine. In one embodiment, the nicotine particles used comprise at least one nicotine salt. In one embodiment, the at least one nicotine salt is nicotine tartrate. In one embodiment, the nicotine particles further comprise at least one sugar. In one embodiment, the at least one sugar is lactose. In one embodiment, the nicotine particles are substantially between 2-5 micron in size. In one embodiment, the concentration of nicotine is about 1.5% to about 20%. In one embodiment the formulation further comprises a stabilizing agent. In one embodiment the formulation is inhaled using an inhaler.

Also described is a method of delivering variable dosages of nicotine to a subject over a number of doses while maintaining a substantially constant level of harshness per inhalation for each dose. The method includes the steps of identifying a concentration of nicotine in a nicotine formulation for a subject to inhale to achieve a desired level of harshness per inhalation, providing a first dose comprising an amount of a formulation comprising nicotine particles having the identified concentration of nicotine, and providing at least one additional dose comprising an amount of a formulation comprising nicotine particles having the identified concentration of nicotine, wherein the amount of the formulation in the at least one additional dose is less than the amount of the formulation in the first dose. In one embodiment, the total dose of nicotine is decreased per dose, while the harshness of the administered doses remains substantially constant.

Also described is a method of delivering reduced dosages of nicotine to a subject over a number of doses, while increasing the level of harshness per inhalation for each dose. The method includes the steps of identifying a concentration of nicotine in a nicotine formulation for a subject to inhale to achieve a desired level of harshness per inhalation, providing a first dose comprising an amount of a formulation comprising nicotine particles having the identified concentration of nicotine, providing at least one additional dose comprising an amount of a formulation comprising nicotine particles having the identified concentration of nicotine, wherein the amount of the formulation in the at least one additional dose is less than the amount of the formulation in the first dose, and providing at least one additional dose comprising an amount of a formulation comprising nicotine particles having the identified concentration of nicotine, wherein the amount of the formulation in the at least one additional dose is less than the amount of the formulation in the first dose.

Also described is a kit for controlling the harshness of inhaled nicotine is described, the kit comprising at least an amount of a nicotine formulation comprising nicotine particles, and an instruction material for the use therewith. In one embodiment, the kit comprises a dry powder inhaler.

Also described is a dry powder nicotine formulation suitable for inhalation comprising nicotine particles, wherein the nicotine particles are substantially between about 1-10 micron in size. In one embodiment, the nicotine particles are substantially between about 2-5 micron in size. In another embodiment, less than about 10% of the nicotine particles are less than about 1 micron in size. In another embodiment, less than about 10% of the nicotine particles are less than about 2 micron in size. In another embodiment, at least about 90% of the nicotine particles are less than about 10 micron in size. In another embodiment, at least about 90% of the nicotine particles are less than about 5 micron in size. In another embodiment, less than about 10% of the nicotine particles are less than about 1 micron in size and wherein at least about 90% of the nicotine particles are less than about 10 micron in size. In another embodiment, less than about 10% of the nicotine particles are less than about 2 micron in size and wherein at least about 90% of the nicotine particles are less than about 5 micron in size.

Also described is a dry powder nicotine formulation suitable for inhalation. The formulation includes a nicotine based component having particles substantially between about 1-10 micron in size, and a cough suppressant component having particles substantially between about 5-10 micron in size. In one embodiment, the cough suppressant component comprises menthol or mint. In another embodiment, the nicotine based component particles are substantially between about 2-5 micron in size and the cough suppressant component particles are substantially between about 5-8 micron in size. In another embodiment, the formulation further includes a cough suppressant component having particles substantially between about 10-200 micron in size. In another embodiment, the cough suppressant component having particles substantially between about 10-200 micron in size comprises menthol or mint. In another embodiment, the formulation includes a flavor component having particles substantially between about 10-1000 micron in size. In another embodiment, the flavor component comprises menthol or mint.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1 is a chart depicting exemplary preparations for achieving various levels of harshness by adjusting one or both of the total amount of powder formulation and the concentration of nicotine in the powder formulation, while maintaining constant the total dose of nicotine delivered within the amount of powder formulation.

FIG. 2 is a chart depicting exemplary preparations for achieving decreasing total doses of nicotine delivered within the amount of powder formulation, by adjusting the total amount of powder formulation containing nicotine particles to maintain a substantially constant level of harshness across the variable doses of nicotine.

FIG. 3 is a chart depicting exemplary preparations for achieving decreasing total doses of nicotine delivered within the amount of powder formulation, by adjusting the total amount of powder formulation containing nicotine particles to increase the level of harshness across the variable doses of nicotine.

DETAILED DESCRIPTION

Definitions

Figure 4:
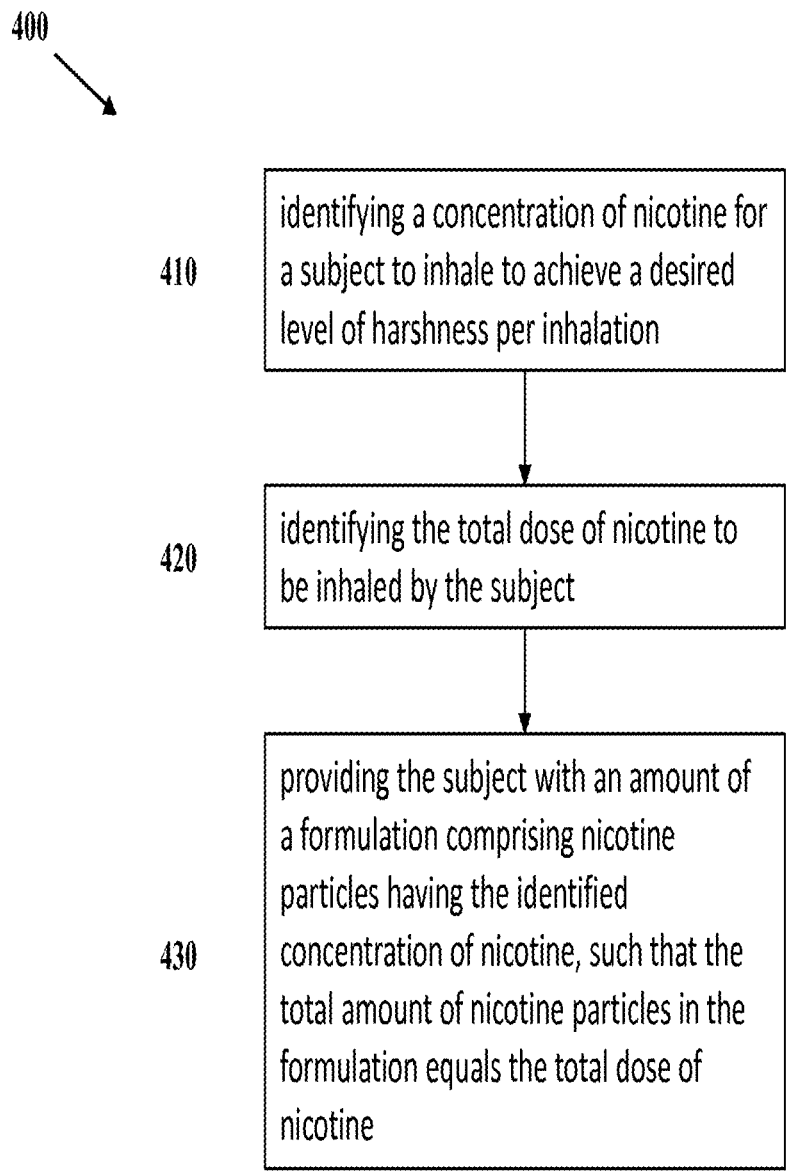
FIG. 4 is a flowchart of an exemplary method of controlling the harshness of nicotine inhaled by a subject.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein the terms "nicotine dose" and "total nicotine dose" refer to the total amount of nicotine to be delivered to a subject in order to achieve a target nicotine blood concentration.

As used herein the term "formulation amount" refers to the total amount of a dry powder formulation packed in a disposable container, such as a capsule or blister pack, to be used with a dry powder inhaler, or to the total amount of a bulk dry powder formulation that can be loaded into a delivery chamber or compartment of a dry powder inhaler. The term also refers to the total amount of a dry powder formulation containing a nicotine dose to be delivered to a subject in order to achieve a particular blood nicotine concentration. Accordingly, the formulation amount includes the total dose of nicotine and may further include any additional pharmaceutically acceptable material, composition or carrier.

As used herein, the term "harshness" refers to the sensation or perception of irritation in a subject's airways after inhaling nicotine particles.

As used herein the term "inhalation" refers to the single act of inhaling an amount of a nicotine dry powder formulation, typically from a dry powder inhaler. The duration of an inhalation can be limited either by the control of the subject over the inhaler, such as by the physical act of continuously inhaling for a period of time and then stopping, or by a physical attribute of the inhaler.

Unless stated otherwise, the described size or size range of a particle should be considered as the mass median aerodynamic diameter (MMAD) of the particle or set of particles. Such values are based on the distribution of the aerodynamic particle diameters defined as the diameter of a sphere with a density of 1 $gm/cm^3$ that has the same aerodynamic behavior as the particle which is being characterized. Because the particles described herein may be in a variety of densities and shapes, the size of the particles is expressed as the MMAD and not the actual diameter of the particles.

The term "pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable" may also refer to a carrier, meaning a medium that does not interfere with the effectiveness of the biological activity of the active ingredient(s) and is not toxic to the host to which it is administered. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "composition" refers to a mixture of at least one compound or molecule useful within the invention with one or more different compound, molecule, or material.

As used herein, an "instructional material" includes a physical or electronic publication, a recording, a diagram, or any other medium of expression which can be used to communicate the usefulness of the composition and method of the invention for its designated use. The instructional material of the kit of the invention may, for example, be affixed to a container which contains the composition or be shipped together with a container which contains the composition. Alternatively, the instructional material may be delivered separately from the container with the intention that the instructional material and the composition be used cooperatively by the recipient.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

In existing nicotine delivery systems and treatment protocols, nicotine blood levels are ultimately controlled by the total dose of inhaled nicotine delivered to the airways of a subject in a specified formulation, and the harshness of the formulation is determined solely by the characteristics of the nicotine. As a consequence to this design, the harshness experienced by the subject during any single inhalation is fixed, meaning the level of harshness cannot be increased or decreased without discontinuing, or improperly administering, the dose. This significantly limits the user experience associated with an inhaled nicotine product.

However, as demonstrated herein, a total dose of nicotine necessary for achieving a specified nicotine blood level can instead be formulated into powder doses having various concentrations within various total formulation amounts. For example, a formulation powder of low nicotine concentration will result in a low level of harshness during inhalation, and may be delivered in a relatively larger total amount of powder in order to achieve the desired blood nicotine level. Similarly, a formulation powder of high nicotine concentration will result in a high level of harshness during inhalation, but can be delivered in a relatively smaller amount of powder in order to achieve the desired blood nicotine level.

Accordingly, the harshness experienced by a subject when inhaling a nicotine-based dry powder formulation can be altered by changing one or both of: 1) the total powder formulation amount, and 2) the concentration of nicotine within the total powder formulation amount. To implement this, dry powder inhalers designed specifically for delivering a powder formulation dose across multiple inhalations may be used. Examples of such dry powder inhalers can be found in co-owned U.S. Patent Application Ser. Nos. 62/147,798; 62/147,803; 62/147,806; 62/147,808; and 62/148,030, the entire disclosures of which are each incorporated by reference herein in their entirety. As contemplated herein, the dry powder formulation may be placed in a sealed storage chamber, such as a capsule or a blister pack, which can be loaded into any of the devices described in the aforementioned, co-owned patent applications.

For example, as shown in FIG. 1, three different formulations are outlined, where each formulation is designed to deliver the same total dose of nicotine (1 mg). To achieve a base level of harshness (Formulation 1), the total dose of nicotine forms part of a 10 mg total formulation amount of powder, which results in a nicotine concentration of 10% in the formulation amount. Assuming that approximately 1 mg of powder can be inhaled per inhalation, this means that about 0.10 mg of nicotine is inhaled per inhalation, and the total dose of nicotine is administered after completion of about 10 inhalations to take up the 10 mg of formulation powder. To achieve a decreased level of harshness (Formulation 2) when delivering 1 mg of nicotine, the total dose of nicotine forms part of a 20 mg total formulation amount of powder, which results in a nicotine concentration of 5% in the formulation amount. Again, assuming that approximately 1 mg of powder can be inhaled per inhalation, this means that about 0.05 mg of nicotine is inhaled per inhalation, and the total dose of nicotine is administered after completion of about 20 inhalations to take up the 20 mg of formulation powder. By taking up a reduced amount of nicotine per inhalation, the user experiences a decreased level of harshness. To achieve an increased level of harshness (Formulation 3) when delivering 1 mg of nicotine, the total dose of nicotine forms part of a 5 mg total formulation amount of powder, which results in a nicotine concentration of 20% in the formulation amount. Again, assuming that approximately 1 mg of powder can be inhaled per inhalation, this means that about 0.20 mg of nicotine is inhaled per inhalation, and the total dose of nicotine is administered after completion of about 5 inhalations to take up the 5 mg of formulation powder. By taking up an increased amount of nicotine per inhalation, the user experiences an increased level of harshness.

By controlling the level of harshness of the inhaled nicotine formulation, the nicotine formulation can be uniquely designed to achieve a specific level of harshness suitable for use with any subject, no matter what tolerance to harshness or irritant a subject may have. In other words, the nicotine powder formulation may be specifically tailored and administered to more accurately mimic the harshness experienced by a subject when smoking. For example, if a subject is being treated with a smoking cessation therapy, the total dose of nicotine can be gradually reduced while maintaining the harshness experienced throughout the process. As shown in FIG. 2, three different formulations are outlined, where each formulation is designed to deliver a different (smaller) total dose of nicotine. Starting with Formulation 4, assume that the targeted level of harshness is achieved by inhalation of 0.1 mg of nicotine per inhalation. Accordingly, 1 mg total dose of nicotine must form part of a 10 mg total formulation amount of powder, which results in a nicotine concentration of 10% in the formulation amount. Assuming that approximately 1 mg of powder can be inhaled per inhalation, this means that about 0.10 mg of nicotine is inhaled per inhalation, and the total dose of nicotine is administered after completion of about 10 inhalations at the desired level of harshness. Formulation 5 is designed for delivery of a total dose of 0.8 mg of nicotine. Accordingly, 0.8 mg total dose of nicotine must form part of an 8 mg total formulation amount of powder, which again results in a nicotine concentration of 10% in the formulation amount. Assuming that approximately 1 mg of powder can be inhaled per inhalation, this means that about 0.10 mg of nicotine is inhaled per inhalation, and the total dose of nicotine is administered after completion of about 8 inhalations at the same level of harshness as was experienced when administering Formulation 4. Likewise, Formulation 6 is designed for delivery of a total dose of 0.6 mg of nicotine. Accordingly, 0.6 mg total dose of nicotine must form part of a 6 mg total formulation amount of powder, which again results in a nicotine concentration of 10% in the formulation amount. Assuming that approximately 1 mg of powder can be inhaled per inhalation, this means that about 0.10 mg of nicotine is inhaled per inhalation, and the total dose of nicotine is administered after completion of about 6 inhalations at the same level of harshness as was experienced when administering Formulations 4 and 5. Thus, a subject can gradually step down the total dose of nicotine administered by subsequently administering Formulations 4-6, while more accurately mimicking the same level of harshness the subject experienced throughout the reduction in delivered nicotine.

In yet another embodiment, the total dose of nicotine can be gradually reduced while also altering the harshness experienced. For example, as shown in FIG. 3, three different formulations are outlined, where each formulation is designed to deliver a different (smaller) total dose of nicotine with slightly increased levels of harshness experienced. Starting with Formulation 7, assume that the initial level of harshness is achieved by inhalation of 0.1 mg of nicotine per inhalation. Accordingly, 1 mg total dose of nicotine must form part of a 10 mg total formulation amount of powder, which results in a nicotine concentration of 10% in the formulation amount. Assuming that approximately 1 mg of powder can be inhaled per inhalation, this means that about 0.10 mg of nicotine is inhaled per inhalation, and the total dose of nicotine is administered after completion of about 10 inhalations at the initial level of harshness. Formulation 8 is designed for delivery of a total dose of 0.8 mg of nicotine with slightly increased harshness. Accordingly, 0.8 mg total dose of nicotine may form part of a 7 mg total formulation amount of powder, which results in a nicotine concentration of about 11.4% in the formulation amount. Assuming that approximately 1 mg of powder can be inhaled per inhalation, this means that about 0.114 mg of nicotine is inhaled per inhalation, and the total dose of nicotine is administered after completion of about 7 inhalations at a slightly increased level of harshness than was experienced when administering Formulation 7. Formulation 9 is designed for delivery of a total dose of 0.6 mg of nicotine with again slightly increased harshness. Accordingly, 0.6 mg total dose of nicotine may form part of a 5 mg total formulation amount of powder, which results in a nicotine concentration of about 12% in the formulation amount. Assuming that approximately 1 mg of powder can be inhaled per inhalation, this means that about 0.12 mg of nicotine is inhaled per inhalation, and the total dose of nicotine is administered after completion of about 5 inhalations at a slightly increased level of harshness than was experienced when administering Formulation 8. Thus, a subject can gradually step down the total dose of nicotine administered by subsequently administering Formulations 7-9, while experiencing an increased level of harshness throughout the reduction in delivered nicotine.

Accordingly, the present invention may include methods for controlling the harshness of nicotine inhaled by a subject, including increasing, decreasing or maintaining the harshness of a nicotine powder formulation inhaled by a subject. For example, as shown in FIG. 4, method 400 includes the steps of identifying a concentration of nicotine for a subject to inhale to achieve a desired level of harshness per inhalation 410, identifying the total dose of nicotine to be inhaled by the subject 420, and providing the subject with an amount of a formulation comprising nicotine particles having the identified concentration of nicotine, such that the total amount of nicotine particles in the formulation equals the total dose of nicotine 430.

Figure 5:
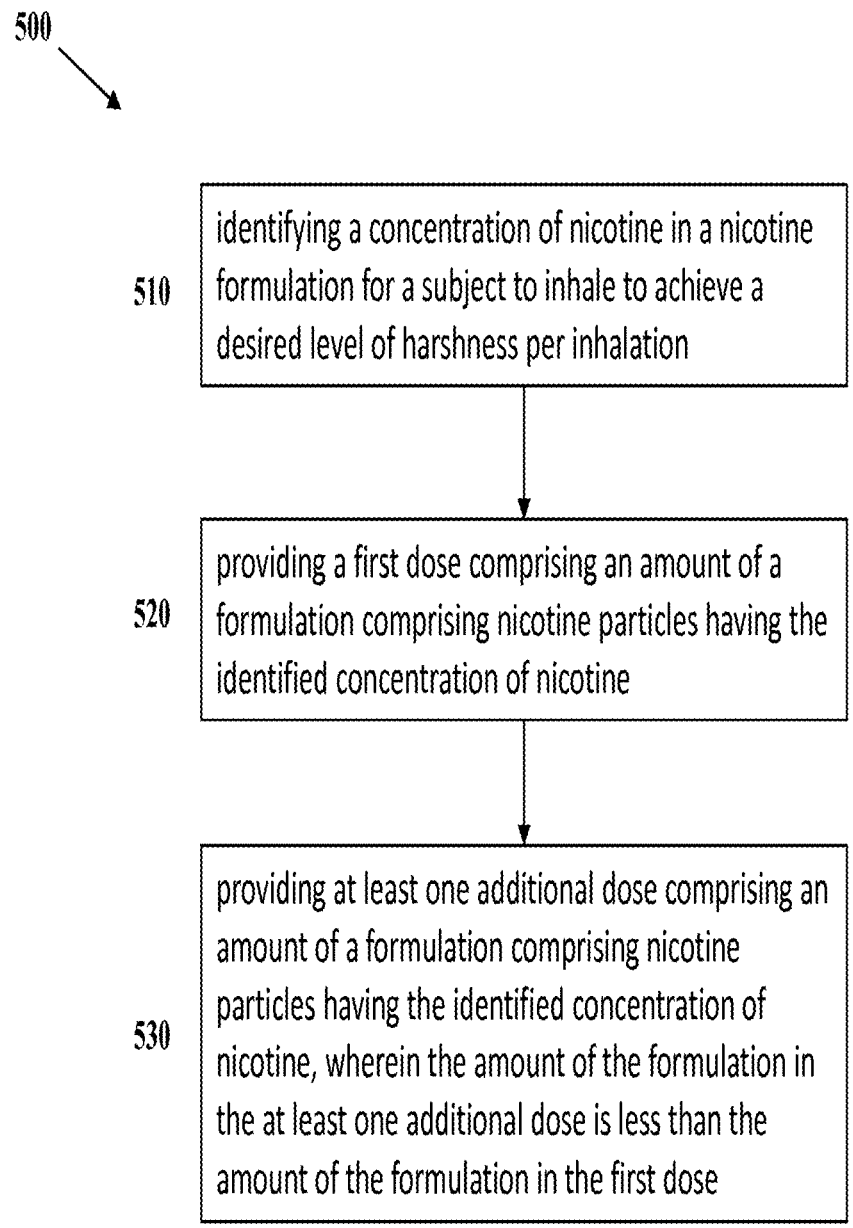
FIG. 5 is a flowchart of an exemplary method for delivering reduced dosages of nicotine to a subject over a number of doses, while maintaining a substantially constant level of harshness per inhalation for each dose.

In another example, as shown in FIG. 5, method 500 may be used for delivering reduced dosages of nicotine to a subject over a number of doses, while maintaining a substantially constant level of harshness per inhalation for each dose. Method 500 may include the steps of identifying a concentration of nicotine in a nicotine formulation for a subject to inhale to achieve a desired level of harshness per inhalation 510, providing a first dose comprising an amount of a formulation comprising nicotine particles having the identified concentration of nicotine 520, and providing at least one additional dose comprising an amount of a formulation comprising nicotine particles having the identified concentration of nicotine, wherein the amount of the formulation in the at least one additional dose is less than the amount of the formulation in the first dose 530.

Figure 6:
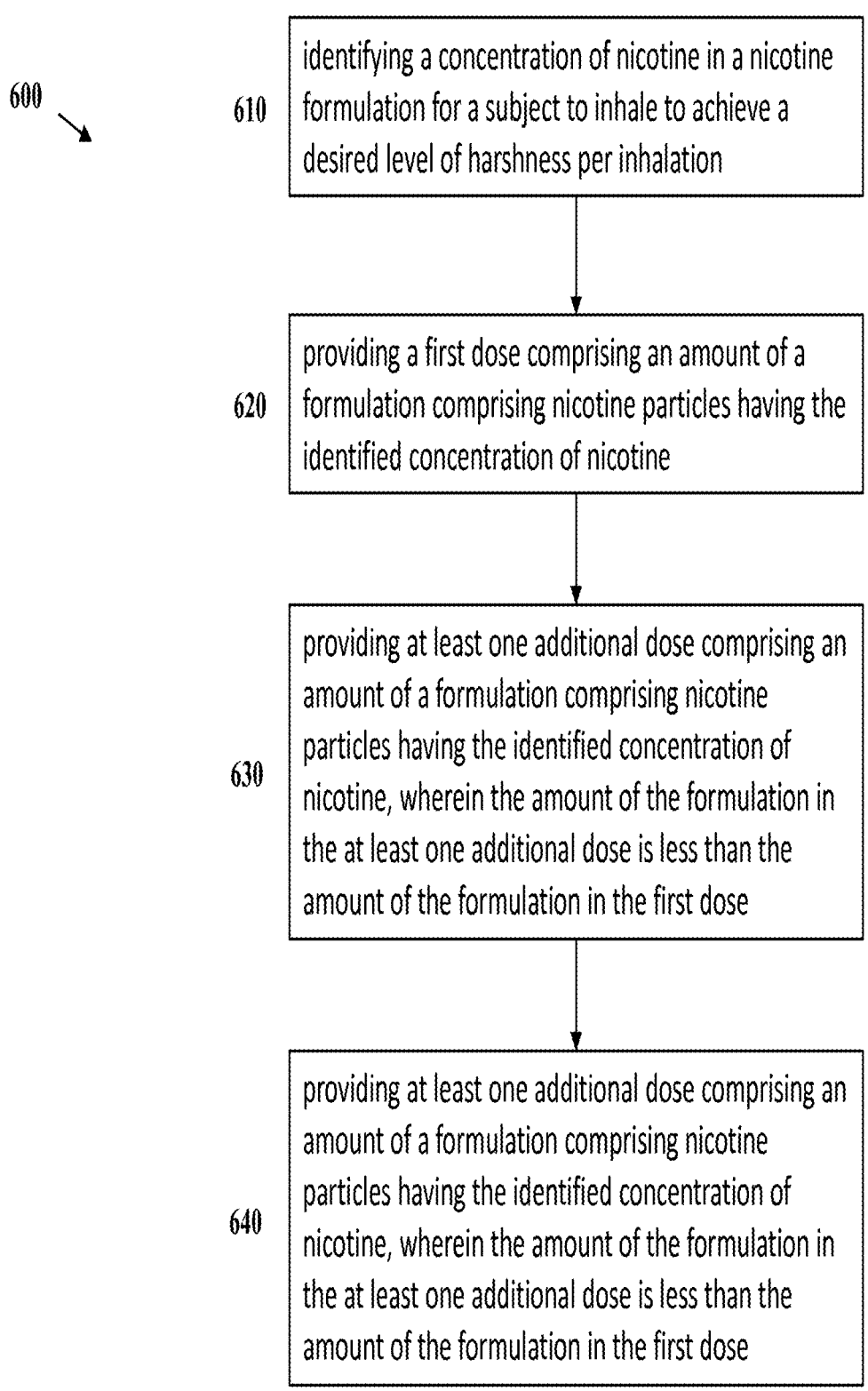
FIG. 6 is a flowchart of an exemplary method for delivering reduced dosages of nicotine to a subject over a number of doses, while increasing the level of harshness per inhalation for each dose.
Figure 7:
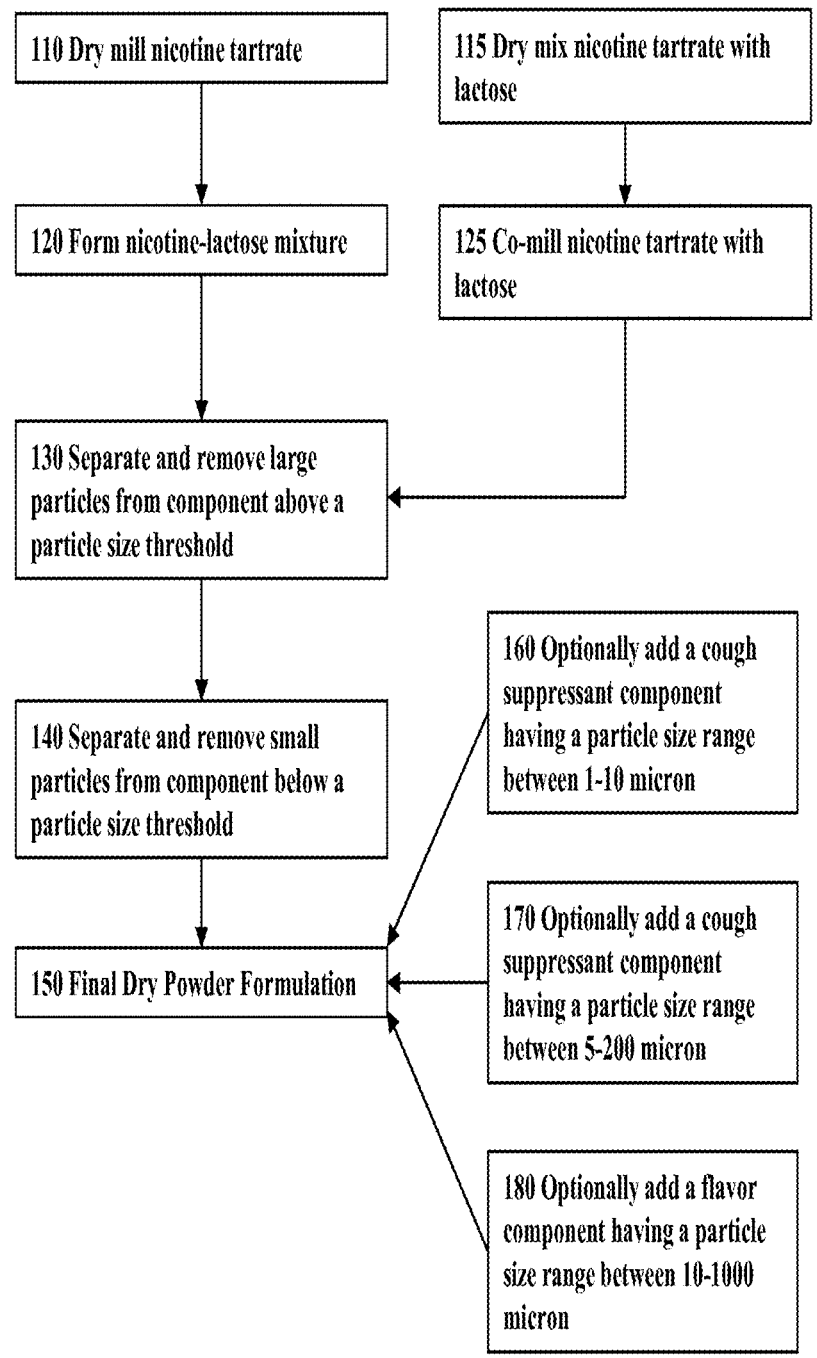
FIG. 7 is a flowchart depicting an exemplary method of manufacturing a formulation of the present invention comprising dry mixing.
Figure 8:
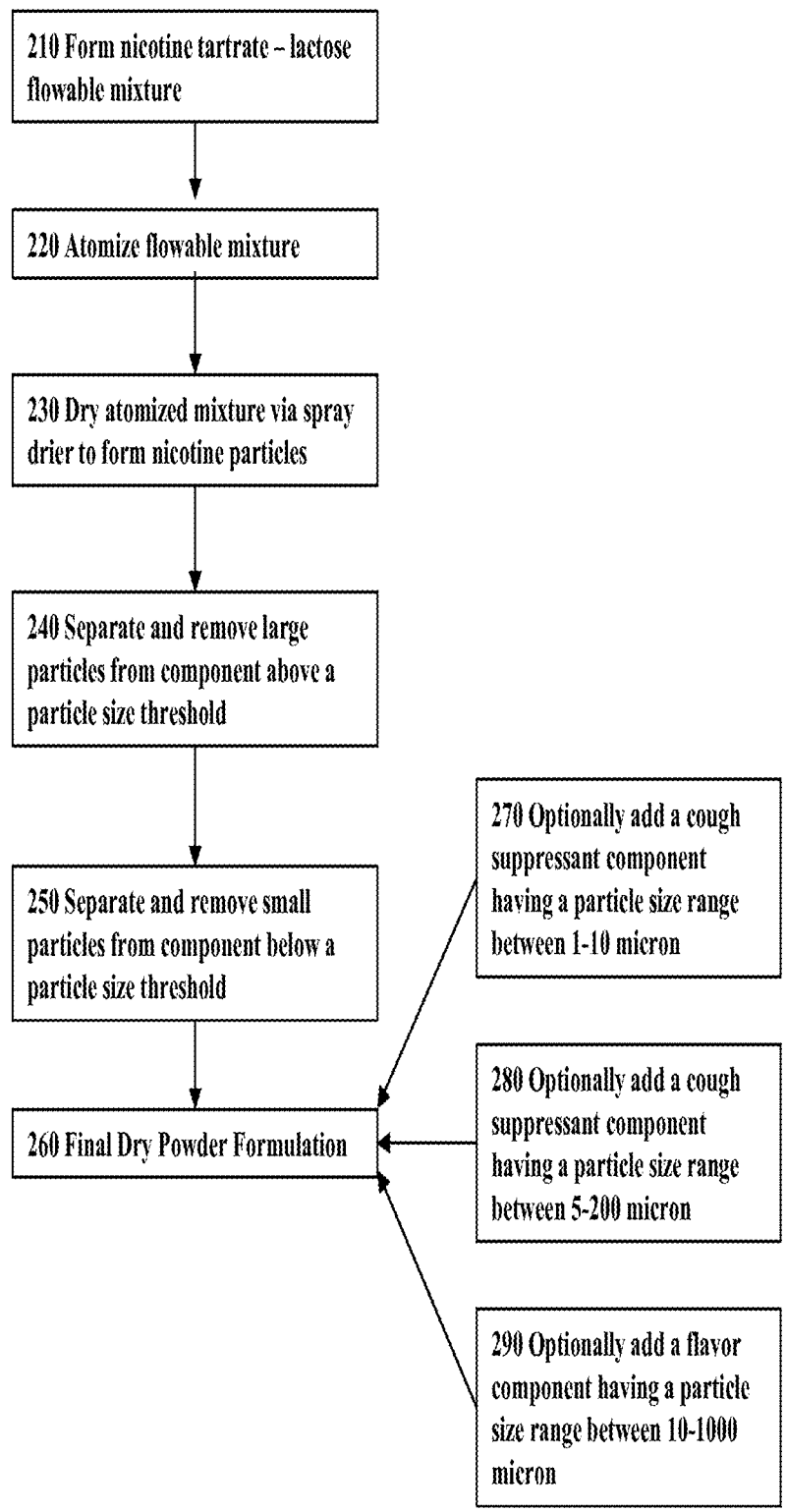
FIG. 8 is a flowchart depicting an exemplary method of manufacturing a formulation of the present invention comprising wet mixing.

In another example, as shown in FIG. 6, method 600 may be used for delivering reduced dosages of nicotine to a subject over a number of doses, while increasing the level of harshness per inhalation for each dose. Method 600 may include the steps of identifying a first concentration of nicotine in a nicotine formulation for a subject to inhale to achieve a first level of harshness per inhalation 610, identifying at least one additional concentration of nicotine in a nicotine formulation for a subject to inhale to achieve a level of harshness per inhalation that is greater than the level of harshness achieved via the first concentration of nicotine 620, providing a first dose comprising an amount of a formulation comprising nicotine particles having the identified first concentration of nicotine 630, and providing at least one additional dose comprising an amount of a formulation comprising nicotine particles having the identified additional concentration of nicotine, wherein the amount of the formulation in the at least one additional dose is less than the amount of the formulation in the first dose 640.

Again, it should be appreciated that any manner of increasing, decreasing or maintaining the total dose of nicotine in a nicotine formulation can be combined with any manner of increasing, decreasing or maintaining the level of harshness experienced by the subject inhaling the nicotine formulation.

As contemplated herein, there is no limitation to the particular formulation amount of powder or the concentration of nicotine within the total formulation amount, but rather, the present invention relates to the ability to alter one or both of these parameters when delivering a total dose of nicotine to a subject via a dry powder inhaler. Further, there is no limitation to the actual amount of powder inhaled per inhalation. Such amounts can be dependent on the functionality of the dry powder inhaler used, or it can be user performance dependent, where a user elects to take a shallower, or deeper, inhalation through the dry powder inhaler used. Furthermore, by administering the total dose of nicotine across multiple inhalations, the subject can more consistently insure uptake of the total dose of nicotine, as any user error occurring during a single inhalation is ultimately corrected through one or more subsequent inhalations.

In one embodiment, a nicotine therapy course may last a number of days. In one embodiment, the course of nicotine therapy lasts between about 7 days, to about 30 days. In another embodiment, the course of nicotine therapy lasts between about 10 days, to about 45 days. In another embodiment, the course of nicotine therapy lasts between about 15 days, to about 60 days. In another embodiment, the course of nicotine therapy lasts between about 30 days, to about 90 days. In a preferred embodiment, the course of nicotine therapy lasts about 30 days. In another preferred embodiment, the course of nicotine therapy lasts about 45 days. In another preferred embodiment, the course of nicotine therapy lasts about 60 days. In another preferred embodiment, the course of nicotine therapy lasts about 90 days.

In another embodiment, the present invention may further include a set of instructions for using or electing a particular nicotine-based powder formulation to achieve a desired level of harshness upon inhalation. For example, the set of instructions may be conveyed to the subject in the form of an "instruction material," such as a pamphlet, manual, or any electronic file format, such as an email, web page, SMS or the like, which can further be part of a kit or associated therewith.

Accordingly, the present invention may further include a nicotine therapy kit, including, but not limited to, smoke cessation kits. In one embodiment, the kit may include a plurality of nicotine-based powder formulation doses contained in a sealed storage chamber, such as a capsule or a blister pack. As contemplated herein, at least two of the formulation doses have equal amounts of a total nicotine, but at different nicotine concentrations. In other embodiments, the kit comprises at least two sets of bulk nicotine-based powder having different concentrations of nicotine, and means for measuring set amounts of the powders, such as a scoop or a graduated measuring container, that can be loaded into the storage chamber of a dry powder inhaler. In other embodiments, the kit comprises a dry powder inhaler with one or more reservoirs or other compartments suitable for holding one or more bulk nicotine-based powder formulations, and further may optionally include a metering mechanism for dispensing or loading a designated amount of formulation for inhalation.

In another embodiment, the kit includes pre-filled powder capsules for a set course of nicotine therapy or treatment, such as for example a 30 day course of treatment. The capsules can be filed with various amounts of powder of various nicotine concentrations, to achieve variable levels of harshness while delivering the same total nicotine dose per the therapy regimen. In other embodiments, the kit includes instructional materials which describe the steps for a method for nicotine therapy, including, but not limited to, smoke cessation therapy. The steps of the method can include a starting dose, regular doses thereafter, such as multiple daily doses for example, and a final dose, to be administered by means of loading the dry powder formulation doses into a dry powder inhaler. The instruction material may also include steps for modulating or electing the harshness of inhalation for any particular administered dosage, such that the subject of the therapy may select the level of harshness experienced by administering the sealed formulation dose corresponding to the level of harshness desired.

In another embodiment, the instruction material may instruct the user on a set number of days course of nicotine therapy, in which the daily nicotine dose may be modulated, while the harshness of the administered doses remains about the same. In one embodiment, the course of nicotine therapy lasts between about 7 days, to about 30 days. In another embodiment, the course of nicotine therapy lasts between about 10 days, to about 45 days. In another embodiment, the course of nicotine therapy lasts between about 15 days, to about 60 days. In another embodiment, the course of nicotine therapy lasts between about 30 days, to about 90 days. In a preferred embodiment, the course of nicotine therapy lasts about 30 days. In another preferred embodiment, the course of nicotine therapy lasts about 45 days. In another preferred embodiment, the course of nicotine therapy lasts about 60 days. In another preferred embodiment, the course of nicotine therapy lasts about 90 days. In one embodiment, the daily nicotine dose is increased daily, while the harshness of the administered doses remains about the same. In another embodiment, the daily nicotine dose is increased daily for a period of time, then decreased daily for a period of time, while the harshness of the administered doses remains about the same. In a preferred embodiment, the daily nicotine dose is decreased daily, while the harshness of the administered doses remains about the same.

In one aspect, the present invention provides compositions and methods related to a dry powder nicotine formulation suitable for inhalation. In one embodiment, the formulation is comprised of nicotine particles and at least one sugar. In one embodiment, the nicotine particles are comprised of a nicotine salt. The present invention also provides methods for producing formulations of the invention.

The present invention relates to dry powder formulations of nicotine, and optionally other selected materials, wherein the nicotine component and optional additional components fall within controlled particle size ranges. For example, in one embodiment, the formulation includes nicotine particles (also referred to herein as the nicotine-based component) sized substantially between about 1-10 microns, based on the MMAD of the particles. In yet another embodiment, the formulation includes nicotine particles sized substantially between about 1-7 microns. In another embodiment, the formulation includes nicotine particles sized substantially between about 2-5 microns. In yet another embodiment, the formulation includes nicotine particles sized substantially between about 2-3 microns. By selectively limiting or excluding nicotine particles below about 1 micron in size, or below about 2 microns in size, the formulations of the present invention remove or at least reduce a subject's ability to exhale nicotine back into the environment, thereby effectively reducing or removing the production of the nicotine contained in second hand smoke. Further, by selectively limiting or excluding non-respirable nicotine particles, the formulations of the present invention reduce unwanted irritation caused by nicotine particles trapped in the larger airways, oro-pharynx, the glottis vocal cords and other anatomic regions more proximal or closer to the mouth. Accordingly, in some embodiments, the smallest particles within the nicotine particle size range are at least about 1 micron, at least about 1.1 microns, at least about 1.2 micron, at least about 1.3 micron, at least about 1.4 micron, at least about 1.5 micron, at least about 1.6 micron, at least about 1.7 micron, at least about 1.8 micron, at least about 1.9 micron, or at least about 2 micron. In some embodiments, the largest particles within the nicotine particle size range are no greater than about 10 micron, no greater than about 7 micron, no greater than about 6 micron, no greater than about 5 micron, no greater than about 4.5 micron, no greater than about 4 micron, no greater than about 3.5 micron, or no greater than about 3 micron. In certain embodiments, no more than about 10% of the nicotine particles are less than about 1 micron. In certain embodiments, no more than about 10% of the nicotine particles are less than about 2 micron. In other embodiments, at least 90% of the nicotine particles are less than about 10 micron. In other embodiments, at least 90% of the nicotine particles are less than about 7 micron. In other embodiments, at least 90% of the nicotine particles are less than about 5 micron. In one embodiment, no more than about 10% of the nicotine particles are less than about 1 micron and at least 90% of the nicotine particles are less than about 10 micron. In one embodiment, no more than about 10% of the nicotine particles are less than about 1 micron and at least 90% of the nicotine particles are less than about 7 micron. In one embodiment, no more than about 10% of the nicotine particles are less than about 2 micron and at least 90% of the nicotine particles are less than about 5 micron. In one embodiment, no more than about 10% of the nicotine particles are less than about 2 micron and at least 90% of the nicotine particles are less than about 3 micron.

As would be understood by a person skilled in the art, the particle size ranges described herein are not absolute ranges. For example, a nicotine particle mixture of the present invention with a size range of about 2-5 microns can contain a portion of particles that are smaller or larger than the about 2-5 micron range. In one embodiment, the particle size value as presented for any particular component of the formulations of the present invention represents a D90 value, wherein 90% of the particles sizes of the mixture are less than the D90 value. In another embodiment, the particle size range represents a particles size distribution (PSD) wherein a percentage of the particles of the mixture lie within the listed range. For example, a nicotine particle size range of about 2-5 microns can represent a mixture of nicotine particles having at least 50% of the particles in the range of about 2-5 microns, but more preferably a higher percentage, such as, but not limited to: 60%, 70%, 80%, 90%, 95%, 97%, 98% or even 99%.

In another example, the formulation of the present invention may optionally include a cough suppressant component having particles sized substantially between 5 and 10 microns. In one embodiment, the cough suppressant component is menthol or mint. In another embodiment, the cough suppressant component may include benzocaine. It should be appreciated that the cough suppressant component can include any compound approved for suppressing cough. By selectively including menthol or mint particles between 5-10 microns, these non-respirable menthol or mint particles can reduce cough by soothing irritation in the subject's upper airways. Accordingly, in some embodiments, the smallest particles within the cough suppressant component particle size range are at least about 5 micron, at least about 6 micron, at least about 7 micron, or at least about 8 micron. In some embodiments, the largest particles within the cough suppressant component particle size range are no greater than about 10 micron, no greater than about 9 micron, no greater than about 8 micron, or no greater than about 7 micron. In certain embodiments, no more than about 10% of the cough suppressant particles are less than about 5 micron. In other embodiments, at least 90% of the cough suppressant particles are less than about 10 micron. In other embodiments, at least 90% of the cough suppressant particles are less than about 8 micron. In one embodiment, no more than about 10% of the cough suppressant particles are less than 4 micron and at least 90% of the cough suppressant particles are less than about 10 micron. In one embodiment, no more than about 10% of the cough suppressant particles are less than about 5 micron and at least 90% of the cough suppressant particles are less than about 8 micron. Although in the preferred embodiment the cough suppressant component is composed of particles substantially in the range of 5-10 micron, the cough suppressant component can comprise particles in a broader range. In one embodiment, the cough suppressant component can comprise particles in the range of 5-25 micron. In another embodiment, the cough suppressant component comprises particles substantially in the range of 5-50 micron. In yet another embodiment, the cough suppressant component comprises particles substantially in the range of 5-100 micron.

In another example, the formulation of the present invention may optionally include a cough suppressant component having particles sized substantially between 10-200 microns. This cough suppressant component can be added to the formulation instead of, or in addition to, the cough suppressant component in the range of 5-10 previously discussed. Accordingly, the formulation of the present invention can comprise two cough suppressant components, wherein each cough suppressant component has a substantially different particle size distribution. The 10-200 micron cough suppressant component may reduce a cough caused by irritation of the oro-pharynx, the glottis vocal cords and other anatomic regions more proximal or closer to the mouth that contain receptors that can trigger cough or trigger other unwanted sensations. As contemplated herein, these larger particles are substantially prohibited from entering the subglottic airways. Accordingly, in some embodiments, the smallest particles within the cough suppressant component particle size range are at least about 10 micron, at least about 12 micron, at least about 20 micron, at least about 30 micron, or at least about 50 micron. In some embodiments, the largest particles within the cough suppressant component particle size range are no greater than about 200 micron, no greater than about 150 micron, no greater than about 120 micron, no greater than about 100 micron, no greater than about 90 micron, or no greater than about 80 micron. In certain embodiments, no more than about 10% of the cough suppressant component particles are less than about 10 micron. In certain embodiments, no more than about 10% of the cough suppressant component particles are less than about 20 micron. In other embodiments, at least 90% of the cough suppressant component particles are less than about 200 micron. In other embodiments, at least 90% of the cough suppressant component particles are less than about 150 micron. In other embodiments, at least 90% of the cough suppressant component particles are less than about 100 micron. In one embodiment, no more than about 10% of the cough suppressant component particles are less than 10 micron and at least 90% of the cough suppressant component particles are less than about 200 micron. In one embodiment, no more than about 10% of the cough suppressant component particles are less than about 12 micron and at least 90% of the cough suppressant component particles are less than about 100 micron. In one embodiment, the cough suppressant component includes menthol or mint particles between about 10-200 microns in size, which may provide a soothing effect in areas of particle impact. In another embodiment, the cough suppressant component having particles between about 10-200 microns in size may include benzocaine. It should be appreciated that the cough suppressant component having particles between about 10-200 microns in size can include any compound approved for suppressing cough. In another example, the addition of at least one component in the formulation of the present invention other than the nicotine component may act to dilute the nicotine containing particles and decrease cough caused by nicotine irritating the oro-pharynx, vocal cords and other anatomic regions proximal to the trachea.

In another example, the formulation of the present invention may optionally include a flavor component having particles sized substantially between about 10-1000 microns. In one embodiment, the flavor component is composed of particles substantially in the range of about 10-200 micron. In a preferred embodiment, the flavor component is composed of particles substantially in the range of about 10-100 micron. This flavor component utilizes such embedded larger particles that may impact the subject in the oral cavity to produce a desired flavor. Further, by limiting such flavor component particles to larger than about 10 microns in size, these particles are limited in their ability to enter into the subject's lungs. Accordingly, in some embodiments, the smallest particles within the flavoring component particle size range are at least about 10 micron, at least about 12 micron, at least about 20 micron, at least about 30 micron, or at least about 50 micron. In some embodiments, the largest particles within the flavoring component particle size range are no greater than about 1000 micron, no greater than about 500 micron, no greater than about 200 micron, no greater than about 150 micron, no greater than about 120 micron, no greater than about 100 micron, no greater than about 90 micron, or no greater than about 80 micron. In certain embodiments, no more than about 10% of the flavor component particles are less than about 10 micron. In certain embodiments, no more than about 10% of the flavor component particles are less than about 20 micron. In other embodiments, at least 90% of the flavor component particles are less than about 1000 micron. In other embodiments, at least 90% of the flavor component particles are less than about 500 micron. In other embodiments, at least 90% of the flavor component particles are less than about 200 micron. In other embodiments, at least 90% of the flavor component particles are less than about 150 micron. In other embodiments, at least 90% of the flavor component particles are less than about 100 micron. In one embodiment, no more than about 10% of the flavor component particles are less than 10 micron and at least 90% of the flavor component particles are less than about 1000 micron. In one embodiment, no more than about 10% of the flavor component particles are less than 10 micron and at least 90% of the flavor component particles are less than about 200 micron. In one embodiment, no more than about 10% of the flavor component particles are less than about 10 micron and at least 90% of the flavor component particles are less than about 100 micron. In one embodiment, the flavor component is menthol. In other embodiments, the flavor component may include tobacco, mint, fruit flavors, or food grade flavorings used in candy or baking. It should be appreciated that the flavor compound may be any flavoring compound known in the art, preferably a regulatory-approved flavoring compound.

As shown in FIG. 2, the present invention includes a dry process or method of producing any one of the formulations described herein. For example, in step 110, nicotine tartrate is dry milled. At step 120, nicotine is mixed with lactose. In some embodiments, the nicotine or nicotine salt is not bound to any other components of the formulation. That is, the formulation contains distinct particles of nicotine or a nicotine salt, and distinct particles of other components of the formulation, such as a sugar. In one embodiment, the nicotine is not bound to the lactose particles. Alternatively, nicotine tartrate and lactose may be first dry mixed, such as in step 115, and co-milled in step 125. At step 130, the particles of the resulting formulation are filtered, such as with a sieve, to remove any particles larger than a threshold size value. At step 140, the particles of the resulting formulation are filtered again to remove any particles smaller than a threshold size value, resulting in the final dry powder formulation. In some embodiments, only one filtering step is needed. In other embodiments, two or more filtering steps are needed. Optionally at step 160, a cough suppressant component may be added to final formulation 150. Step 160 may contain any number of processing steps needed to obtain the desired particle size (e.g., 1-10 micron) for the cough suppressant component being added. Optionally at step 170, a cough suppressant component may be added to final formulation 150. Step 170 may contain any number of processing steps needed to obtain the desired particle size (e.g., 10-200 micron) for the cough suppressant component being added. Optionally at step 180, a flavor component may be added to final formulation 150. Step 180 may contain any number of processing steps needed to obtain the desired particle size (e.g., 10-1000 micron) for the flavor component being added.

As shown in FIG. 3, the present invention also includes a wet process or method of producing any one of the formulations described herein. For example, in step 210, nicotine tartrate is admixed with a carrier, such as lactose, to form a flowable mixture. At step 220, the mixture is atomized. At step 230, the mixture is dried, such as via a spray drier. Alternatively, the process may optionally be performed via fluid bed drying, wherein nicotine tartrate can instead be spray dried onto the lactose. At step 240, the resulting nicotine particles are filtered, such as with a sieve, to remove any particles larger than a threshold size value. At step 250, the resulting nicotine particles are filtered again to remove any particles smaller than a threshold size value, resulting in the final dry powder formulation. In some embodiments, only one filtering step is needed. In other embodiments, two or more filtering steps are needed. Optionally at step 270, a cough suppressant component may be added to final formulation 260. Step 270 may contain any number of processing steps needed to obtain the desired particle size (e.g., 1-10 micron) for the cough suppressant component being added. Optionally at step 280, a cough suppressant component may be added to final formulation 260. Step 280 may contain any number of processing steps needed to obtain the desired particle size (e.g., 10-200 micron) for the cough suppressant component being added. Optionally at step 290, a flavor component may be added to final formulation 260. Step 290 may contain any number of processing steps needed to obtain the desired particle size (e.g., 10-1000 micron) for the flavor component being added.

In one embodiment, the nicotine-based component may include nicotine and a pharmaceutical grade sugar prepared as solid discrete flowable particles, which may be entrained in the air inhaled by a subject so as to travel to the alveoli and smaller airways of the lungs. Further, the dried nicotine-sugar particles may be filtered, such as via one or more sieving steps, to isolate and segregate the desired particle sizes from those particles being removed.

In one embodiment, initial particles of the nicotine-based component may be produced via the methods as described in U.S. Patent Application Publication No. 20120042886, which is incorporated by reference herein in its entirety. For example, in a first step, nicotine and a pharmaceutical grade sugar, such as lactose, can be mixed with a liquid carrier so as to form a flowable mixture.

As contemplated herein, any form of nicotine may be used as the nicotine-based component. Preferably the form of nicotine used is one which achieves the fast uptake into the lungs of the patient. A form of nicotine which can be milled, or co-milled with a sugar or other components, is preferable. In another embodiment, the nicotine is blended with a sugar or other components. In one embodiment, the nicotine is a salt, which, at room temperature, is a solid. The nicotine may further be a pharmacologically active analog or derivative of nicotine or substance that mimics the effect of nicotine, either alone or in combination with other active substances. If the nicotine is a base, then it may be added to a liquid carrier, such as water, and mixed to produce a generally homogeneous liquid mixture, which can then be dried by various method to form a dry particulate formulation. In other embodiments a form of nicotine which is soluble in or miscible with a liquid carrier may also be used. For example, the nicotine may be a nicotine base, which, at room temperature, is a liquid that is miscible in water. Alternatively, the nicotine base may be an oil formulation.

Accordingly, in one embodiment, nicotine is present in the formulation as a free base. In another embodiment, the formulation may comprise a nicotine salt. In one such embodiment, the nicotine salt is nicotine tartrate. In another embodiment, the nicotine salt is nicotine hydrogen tartrate. In other embodiments, the nicotine salt can be prepared from any suitably non-toxic acid, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-toluenenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like.

As contemplated herein, the sugar is an inhalable sugar, and is generally solid at room temperature. The sugar can be milled into a particulate formulation, either by itself, or co-milled with a nicotine component. The sugar may also be soluble in a liquid carrier, such as water. Without limitation, examples of suitable sugars are lactose, sucrose, raffinose, trehalose, fructose, dextrose, glucose, maltose, mannitol, or combinations thereof. In one embodiment, the sugar is lactose. In another embodiment, the lactose is coarse lactose. In another embodiment, the sugar is alpha monohydrate lactose. The sugar may be a natural or a synthetic sugar, and may include any analogs or derivatives of sugars. It should be appreciated that any form of sugar approved as an excipient may be used as a carrier in the production of the nicotine-based component. While not required, the sugar is preferably of a pharmaceutical grade as would be understood by those skilled in the art. Preferably, the pharmaceutical grade sugar used to be milled by itself, co-milled with a nicotine component or to create the flowable mixture is a non-spheronized sugar. The pharmaceutical grade sugar may be prepared in a non-spheronized form prior to dry or wet admixture with nicotine. For example, the pharmaceutical grade sugar may be first prepared in a non-spheronized form by freeze drying, milling, micronizing or the like. In certain embodiments, the pharmaceutical grade sugar may be subjected to milling, bashing, grinding, crushing, cutting, sieving or other physical degradation process as understood by those skilled in the art, which ultimately reduces the particle size of the sugar and results in a non-spheronized sugar.

In various embodiments, the formulation can further comprise any pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. In one embodiment, the formulation is further comprised of a stabilizing agent. Each material must be "acceptable" in the sense of being compatible with the other ingredients of the formulation, including nicotine, and not injurious to the subject. Some materials that may useful in the formulation of the present invention include pharmaceutically acceptable carriers, for example sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter, lecithin, and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. Other pharmaceutically acceptable materials that can be useful in the formulation include any and all coatings, antibacterial and antifungal agents, and absorption delaying agents, and the like that are compatible with the activity of nicotine or any other compound useful within the invention, and are physiologically acceptable to the subject. Supplementary active compounds, including pharmaceutically acceptable salts of those compounds, may also be incorporated into the compositions. Other additional ingredients that may be included in the compositions used in the practice of the invention are known in the art and described, for example in Remington's Pharmaceutical Sciences (Genaro, Ed., Mack Publishing Co., 1985, Easton, Pa.), which is incorporated herein by reference.

Any method of blending particles in and for the methods and formulations of the present invention is contemplated here. The blending can be conducted in one or more steps, in a continuous, batch, or semi-batch process. For example, if two or more excipients are used, they can be blended together before, or at the same time as, being blended with the pharmaceutical agent microparticles.

The blending can be carried out using essentially any technique or device suitable for combining the microparticles with one or more other materials (e.g., excipients) effective to achieve uniformity of blend. The blending process may be performed using a variety of blenders. Representative examples of suitable blenders include V-blenders, slant-cone blenders, cube blenders, bin blenders, static continuous blenders, dynamic continuous blenders, orbital screw blenders, planetary blenders, Forberg blenders, horizontal double-arm blenders, horizontal high intensity mixers, vertical high intensity mixers, stirring vane mixers, twin cone mixers, drum mixers, and tumble blenders. The blender preferably is of a strict sanitary design required for pharmaceutical products. Tumble blenders are often preferred for batch operation. In one embodiment, blending is accomplished by aseptically combining two or more components (which can include both dry components and small portions of liquid components) in a suitable container. One example of a tumble blender is the TURBULA™, distributed by Glen Mills Inc., Clifton, N.J., USA, and made by Willy A. Bachofen AG, Maschinenfabrik, Basel, Switzerland.

For continuous or semi-continuous operation, the blender optionally may be provided with a rotary feeder, screw conveyor, or other feeder mechanism for controlled introduction of one or more of the dry powder components into the blender.

The milling step is used to fracture and/or deagglomerate the blended particles, to achieve a desired particle size and size distribution, as well as to enhance distribution of the particles within the blend. Any method of milling can be used to form the particles of the invention, as understood by one of ordinary skill in the art. A variety of milling processes and equipment known in the art may be used. Examples include hammer mills, ball mills, roller mills, disc grinders, jet milling and the like. Preferably, a dry milling process is used.

As contemplated herein, any liquid carrier may be used in the wet process. Preferably, the liquid carrier is one in which both the pharmaceutical grade sugar and the nicotine tartrate or the nicotine base are soluble. For example, in one embodiment, the liquid carrier is water. While water is the preferred liquid carrier, other liquids in combination with or in place of water may be used. For example, the liquid carrier may comprise a mixture of an alcohol and water to form an azeotropic liquid carrier. If an alcohol is used, the alcohol is preferably a primary alcohol. In one embodiment, the alcohol is preferably a lower alkyl alcohol (i.e. $C_1$ to $C_5$), such as ethanol. In such embodiments, any ratio of water to alcohol may be used, and may be determined when balancing the solubility of the mixture components with the desired drying rate of the final mixture. In some embodiments, the ratio of alcohol to water in the liquid carrier may be from about 1:1 to 1:10, preferably from about 1:2 to 1:8 and more preferably from about 1:5 to 1:7 parts by weight. Accordingly, the liquid carrier may be any liquid or liquids with which nicotine may be admixed with sugar to form a flowable mixture which is preferably of a generally uniform composition.

It should be appreciated that there are no limitations to the ratio of nicotine to sugar, or other components used, and the actual ratio used will be based on the concentration of nicotine desired in the nicotine based component particles. In one embodiment the percentage of nicotine in the formulation is between 1.5% and 20%. In one embodiment, the percentage of nicotine in the formulation is between 0.5% and 5%. In some embodiments, the percentage of nicotine in the formulation is between 1.5% and 2.5%. In other embodiments, the percentage of nicotine in the formulation is between 0.5% and 2.5%. In yet other embodiments the percentage of nicotine in the formulation is between 1.5% and 5%. In one embodiment, the percentage of nicotine in the formulation is about 2.5%. In another embodiment, the percentage of nicotine in the formulation is about 5%. In other embodiments the concentration of nicotine is between about 5-10%. In another embodiment, the percentage of nicotine in the formulation is about 10%. In one embodiment the ratio of sugar to nicotine in the dry mixture or the wet flowable mixture may vary from about 1:100 to about 100:1, or from about 3:7 to about 3:2 or alternatively, from about 4:6 parts by weight. Further, the concentration of sugar in the dry mixture or the wet flowable mixture may vary from about 1 to about 10 w/v (g/100 ml), from about 2 to about 5 w/v (g/100 ml) or from about 3% w/v (g/100 ml).

As mentioned previously, in the wet process the nicotine-sugar flowable mixture is dried, such as via a spray drier, to produce composite particles of nicotine-sugar that are suitable for delivery to the alveoli and lower airways of a subject. It should be appreciated that there is no limitation to the method of drying the flowable mixture. While a preferred method utilizes a spray drier, other drying techniques capable of producing appropriately sized particles may be used, such as fluidized bed drying. In one embodiment, the mixture is finely divided via passage through an orifice upon on entry to a spray dryer. In another embodiment, the flowable mixture may be passed through an atomizer, such as a rotary atomizer, to feed the flowable liquid into a spray dryer. Further still, any rate of drying may be used (e.g., slow or rapid rate drying), provided such rate of drying results in the formation of dry particles of the desired size range. Prior to the segregation of the desired particle size of the nicotine-based component, the resultant particles formed via the spray drier may have a particle size from about 0.1 to about 5 micron.

Additional segregation/filtering of selected particle sizes may be performed both in the dry and the wet process. In the wet process, the operating conditions of the spray dryer may be adjusted so to produce particles which are sized so as to be able to travel to the alveoli and smaller airways of the lungs. For example, a rotary atomizer may be operated at a liquid feed rate from about 2 to about 20 ml/min, or from 2 to about 10 ml/min, or from about 2 to about 5 ml/min. Further, the rotary atomizer may be operated from about 10,000 to about 30,000 rpm, from about 15,000 to about 25,000 rpm, or from about 20,000 to about 25,000 rpm. It should be appreciated that particles of various sizes may be obtained by spray drying, and particles having the desired particle size may be more specifically selected when filtered, such as via one or more sieving steps, as described elsewhere herein. The spray dryer may be operated at temperatures sufficiently high to cause the liquid carrier to rapidly evolve without raising the temperature of the sugar and nicotine within the mixture to a point at which these compounds begin to degrade. Accordingly, the spray dryer may be operated with an inlet temperature from about 120° C. to about 170° C., and an outlet temperature from about 70° C. to about 100° C.

It should be appreciated that the nicotine-based component particles may be spherical or of any other shape desired. In one embodiment of the wet process, by evolving the liquid carrier sufficiently rapidly during the spray drying process, the particles may be produced with an uneven or a "dimpled" surface. In such embodiments, the uneven surface may produce a relative turbulence as the particles travel through the air, thus providing the particles with aerodynamic lift. In such embodiments, particles having such shape may be more readily entrained, and to remain entrained, in the air inhaled by a subject, thereby improving the ability of the nicotine-based component particles to travel to the alveoli and smaller airways.

As mentioned previously, the present invention includes formulations having components characterized by particular particle size ranges. For example, the formulations of the present invention can include nicotine-based particles sized substantially between about 1-10 microns, and preferably between about 2-5 microns. In other embodiments, the formulations can optionally include a cough suppressant component (such as menthol or mint) having particles in the size range of about 1-100 microns. In other embodiments, the formulations can optionally include a second cough suppressant component having particles in the size range of about 10-200 microns. In further embodiments, the formulations can include a flavor component (such as menthol or mint) having particles in the size range of about 10-1000 microns.

As contemplated herein, the particles of the present invention can be produced in relatively narrow size ranges via the use of at least one sieving step. In such an embodiment, the sieving step includes using a sieve corresponding to the minimum or maximum of the desired particle size range to eliminate particles from the mixture that are smaller or bigger than the desired range. For example, to obtain nicotine particles in the range of about 1-5 microns, a mixture of nicotine particles produced using the milling process described herein can be provided. The mixture of nicotine particles will have a size distribution that is dependent on the milling conditions used and/or the characteristics of the input mixture to the mill. The mixture of nicotine particles can first be passed through a 5 micron sieve, wherein substantially all of the particles smaller than 5 microns pass through the sieve and are collected. The particles passing through the sieve can then transferred to a 1 micron sieve, wherein substantially all of the particles greater than 1 micron do not pass through the sieve. The particles greater than 1 micron can be collected from the sieve, wherein the collected particles will be substantially sized in the range of 1-5 microns. Accordingly, such a process can be used to narrow the range of any mixture of particles to any of the desired particle size ranges as described hereinthroughout.

In another embodiment, a mixture of particles can be provided that substantially meets either the minimum or maximum criteria of the desired particle size range. For example, if a nicotine particle size range of about 2-5 microns is desired, a mixture of nicotine particles can be provided wherein substantially all of the particles are less than 5 microns. Such a mixture can be produced by modifying the milling conditions, or when the particles are spray dried, by milling the spray dried material to result in a mixture of particles that are generally less than 5 microns. The mixture can then be transferred through a 2 micron sieve, wherein the particles not passing through the sieve are collected, and wherein the collected particles are substantially within the desired 2-3 micron range.

It is contemplated that the percentage of particles falling within the desired particle size range for any of the components of the formulation of the present invention can be dependent on the technique used to produce that component. For example, if the targeted size of the nicotine component is in the range of 2-5 micron, it is understood that greater than 90% of that component will fall within the desired range when using a spray drying production technique on a relatively small scale. However, using a relatively large scale milling production technique may only yield greater than 70% of the nicotine component within such a targeted range.

As mentioned previously, the formulation may optionally include a cough suppressant component, wherein the particles of the cough suppressant component are sized between about 5 and 10 micron. By selectively including menthol or mint particles sized between about 5-10 microns, these non-respirable menthol or mint particles can reduce cough by soothing irritation in the subject's larger airways as well as the oro-pharynx. In another example, the formulation of the present invention may optionally include a cough suppressant component having particles sized substantially between about 10-200 microns. This cough suppressant component may reduce a cough caused by irritation of the oro-pharynx, the glottis vocal cords and other anatomic regions more proximal or closer to the mouth that contain receptors that can trigger cough or trigger other unwanted sensations. As contemplated herein, these larger particles do not enter the sub-glottic airways because of their momentum.

In one embodiment, the cough suppressant component of either the 5-10 or 10-200 micron ranges comprises menthol or mint. Further, it should be appreciated that any other cough suppressant compounds may be used instead of or in addition to menthol or mint, without limitation.

As contemplated herein, any form of menthol or mint, such as a solid form of menthol or mint can be used for processing into menthol or mint particles useful within the present invention. Non-limiting examples of solid forms of menthol or mint include powders, crystals, solidified distillate, flakes, and pressed articles. In one embodiment, menthol or mint is in the form of crystals. Menthol or mint can be processed into particles of a size ranging from about 5 μm to about 10 μm using any method known in the art. In some embodiments, menthol or mint is admixed with further liquid or solid additives for processing. Particulate additives can furthermore also be used. In one embodiment, menthol or mint is admixed with silicon dioxide. In another embodiment, menthol or mint is admixed with a sugar, such as lactose. In some embodiments of the wet process, the menthol or mint is processed in a liquid carrier.

As contemplated herein, any liquid carrier may be used in the process of producing the menthol or mint particles. In one embodiment, the liquid carrier is water. Preferably, the liquid carrier is one in which the menthol or mint is soluble. Accordingly, the liquid carrier may be any liquid or liquids with which menthol or mint, either alone or in combination with an additional component, forms a flowable mixture which is preferably of a generally uniform composition.

The menthol or mint flowable mixture may be dried, such as via a spray drier, to produce composite particles of menthol or mint, alone or in combination with an additional component, that are suitable for delivery to the alveoli and lower airways of a person. It should be appreciated that there is no limitation to the method of drying the flowable mixture. Examples of methods for drying the flowable mixture include, but are not limited to, spray drying, vacuum drying, and freeze drying. Further still, any rate of drying may be used (e.g., slow or rapid rate drying), provided such rate of drying results in the formation of dry particles of the desired size range.

As mentioned previously, the formulation may optionally include a flavor component, wherein the particles of the flavor component are sized between about 10 and about 1000 micron. In one embodiment, the flavor component comprises menthol or mint and may be produced as previously described herein. When other flavoring compounds are used, any known processing steps suitable for such compounds may be used to produce the flavoring component within the desired particle size range of about 10-1000 micron.

In various embodiments, the relative weight percentage of each component in the formulation of the present invention can be varied to achieve different characteristics. Thus, as one skilled in the art would understand, the relative weight percentages of the components can be modified for various reasons, for example, but not limited to: achieving a certain level of blood nicotine concentration while modulating the level of harshness on the airways of the subject, achieving a certain level of harshness while modulating the level of satisfaction perceived by the subject of the therapy, achieving better uptake of nicotine in the lungs of the patient, achieving faster blood nicotine kinetics, optimizing the cough suppressant performance of the formulation, varying or improving the taste of the formulation, and adjusting the relative dose of nicotine. In certain embodiments, the formulation can be about 1-20% by weight flavor component, with a preferred weight of 1-5% flavor component. In certain embodiments, the formulation can be about 1-10% by weight cough suppressant, with a preferred weight of 1-2.5% cough suppressant. In various embodiments, the remaining portion of the formulation, aside from any flavor components, cough suppressant components, carriers, or other components, is the nicotine component.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of controlling the harshness of nicotine inhaled by a subject, the method comprising the steps of:
    identifying a concentration of nicotine for a dry powder formulation comprising nicotine particles for a subject to inhale based on a desired level of harshness per inhalation, the nicotine particles comprising nicotine salt and sugar;
    providing the subject with a first dose comprising a first amount of the formulation having the identified concentration of nicotine;
    providing the subject with a second dose comprising a second amount of the formulation, the second dose comprising a lower amount of nicotine than the first dose; and
    providing the subject with a third dose comprising a third amount of the formulation, the third dose comprising a lower amount of nicotine than the second dose,
    wherein at least one of the second and third doses has a concentration that is higher than the identified concentration of the first dose to increase the harshness of the nicotine inhaled by the subject.

2. The method of claim 1, wherein the identified concentration of nicotine is selected from concentrations ranging from 0.7 wt-% to 10 wt-%.

3. The method of claim 1, wherein the method is a method of smoking cessation therapy.

4. The method of claim 1, wherein the nicotine particles comprise trehalose.

5. The method of claim 1, wherein the nicotine particles are less than 5 micron in size.

6. The method of claim 1, wherein the formulation further comprises cough suppressant particles.

7. The method of claim 1, wherein the formulation is delivered to a subject via a dry powder inhaler.

8. A method of delivering reducing dosages of nicotine to a subject by inhalation, the method comprising:
    identifying a first concentration of nicotine for a nicotine dry powder formulation to achieve a desired first level of harshness per inhalation, the nicotine dry powder formulation comprising nicotine particles comprising nicotine salt and sugar;
    providing a first dose to the subject, the first dose comprising the nicotine dry powder formulation having the identified first concentration of nicotine;
    providing a second dose to the subject, the second dose being lower than the first dose and having a second concentration of nicotine which is greater than the first concentration of nicotine; and
    providing a third dose to the subject, the third dose being lower than the second dose and having a third concentration of nicotine which is greater than the second concentration of nicotine.

9. The method of claim 8, wherein the identified concentration of nicotine is selected from concentrations ranging from 0.7 wt-% to 10 wt-%.

10. The method of claim 8, wherein the method is a method of smoking cessation therapy.

11. The method of claim 8, wherein the nicotine particles further comprise trehalose.

12. The method of claim 8, wherein the nicotine particles are less than 5 micron in size.

13. The method of claim 8, wherein the formulation further comprises cough suppressant particles.

14. The method of claim 8, wherein the formulation is delivered to a subject via a dry powder inhaler.

* * * * *